US 8,101,757 B2

(12) United States Patent
Wang et al.

(10) Patent No.: US 8,101,757 B2
(45) Date of Patent: Jan. 24, 2012

(54) PROCESSES FOR THE PREPARATION OF NORMORPHINAN SALTS

(75) Inventors: Peter X. Wang, Clarkson Valley, MO (US); Tao Jiang, St. Louis, MO (US); Gary L. Cantrell, Troy, IL (US); David W. Berberich, St. Peters, MO (US); Jian Bao, Chesterfield, MO (US); Bobby N. Trawick, Florissant, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 586 days.

(21) Appl. No.: 12/316,887

(22) Filed: Dec. 17, 2008

(65) Prior Publication Data

US 2009/0156819 A1 Jun. 18, 2009

Related U.S. Application Data

(60) Provisional application No. 61/014,105, filed on Dec. 17, 2007.

(51) Int. Cl.
*C07D 489/02* (2006.01)
*C07D 489/08* (2006.01)
(52) U.S. Cl. .......................................... 546/45; 546/44
(58) Field of Classification Search ................ 546/45, 546/44
See application file for complete search history.

(56) References Cited

U.S. PATENT DOCUMENTS 3,905,981 A * 9/1975 Olofson et al. ................ 546/44
4,141,897 A * 2/1979 Olofson et al. ................ 546/45
4,368,326 A 1/1983 Rice

FOREIGN PATENT DOCUMENTS

| EP | 0 158 476 | 10/1985 |
| WO | WO 2006/084389 | 8/2006 |
| WO | WO 2007/137782 | 12/2007 |

OTHER PUBLICATIONS

Ninan et al., "An improved synthesis of noroxymorphone", Tetrahedron, vol. 48, No. 32, 1992, pp. 6709-1716, XP002144371.
Schmidhammer et al., "Synthesis and Biological Evaluation of 14-Alkoxymorphinans Part 4 Opioid Agonists and Partial Opioid Agonists in a Series of N-(Cyclobuthylmethyl)-14-Methoxymorphinan-6-Ones", Helvetica Chimica Acta, vol. 72, 1989, pp. 1233-1240, XP009077767.
Greiner et al., "Synthesis and Biological Evaluation of 14-Alkoxymorphinans . . . ", J. Med. Chem., 2003, 46, gps. 1758-1763, XP002527613.

* cited by examiner

*Primary Examiner* — Charanjit Aulakh

(57) ABSTRACT

The invention provides a process for the conversion of opioid derivatives into normorphinan compounds useful for making "nal" compound analgesics and antagonists. In particular, the process may be used for the production of pure normorphinan salts from crude opioid substrates.

25 Claims, No Drawings

PROCESSES FOR THE PREPARATION OF NORMORPHINAN SALTS

CROSS-REFERENCE TO RELATED APPLICATION

This application claims priority from Provisional Application Ser. No. 61/014,105 filed on Dec. 17, 2007, which is hereby incorporated by reference in its entirety.

FIELD OF THE INVENTION

The present invention generally relates to processes for the production of pure normorphinan salts from crude opioid substrates.

BACKGROUND OF THE INVENTION

Noroxymorphone is a morphinan intermediate useful for making a series of biologically important "nal" compounds, including naltrexone, naloxone, nalmefene, and nalbuphine. As demands on these APIs (active pharmaceutical ingredients) have increased, there has been a greater need for noroxymorphone to be produced more efficiently and at higher purity.

Noroxymorphone has historically been obtained by hydrolyzing dec-noroxymorphone in water with 30-40% sulfuric acid at 95 to 110° C. for 30 to 40 hours. See, e.g., "Noroxymorphone from morphine." Wallace, Rebecca A. (Mallinckrodt, Inc., USA). Eur. Pat. Appl. EP158476 (1985). There are several problems associated with this process including: (a) the starting materials (i.e. dec-noroxymorphone) have very poor solubility; (b) the hydrolysis rate is very slow (the reaction would take 30 to 40 hours to complete); (c) the oxidative properties of the hydrolyzing agent (i.e. sulfuric acid), and prolonged heating necessary for the hydrolysis to occur results in the decomposition of the noroxymorphone product; and, (d) the overall reaction results in noroxymorphone at low yield and high impurity. A need therefore exists for a process for the conversion of opioid derivatives to key morphinan compounds useful for making analgesics and antagonists.

SUMMARY OF THE INVENTION

One aspect of the invention encompasses a process for the preparation of compound 2 from compound 1 according to the following reaction:

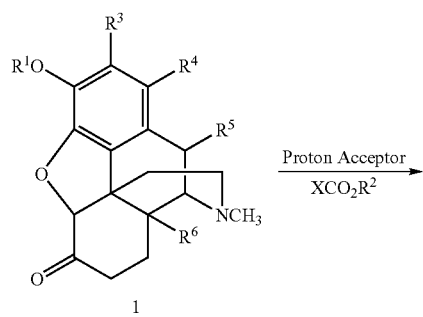

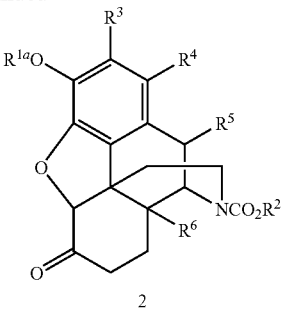

wherein:
- $R^1$ is selected from the group consisting of hydrogen, hydrocarbyl and substituted hydrocarbyl;
- $R^{1a}$ is an oxygen protecting group;
- $R^2$ is selected from the group consisting of hydrocarbyl, and substituted hydrocarbyl;
- $R^3$, $R^4$, $R^5$, and $R^6$, are independently selected from the group consisting of hydrogen, halogen, hydroxyl, methoxy, {—}$OR^8$, hydrocarbyl, and substituted hydrocarbyl;
- $R^8$ is selected from the group consisting of hydrocarbyl, and substituted hydrocarbyl; and
- X is halogen selected from the group consisting of Cl, and Br.

Another aspect of the invention provides a process for the preparation of compound 3 from compound 2 according to the following reaction:

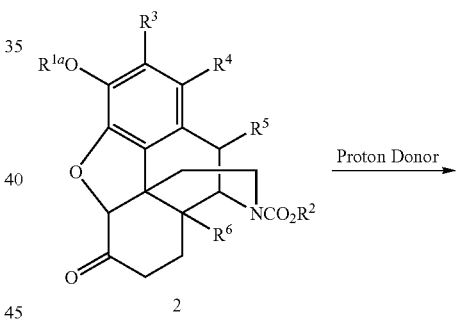

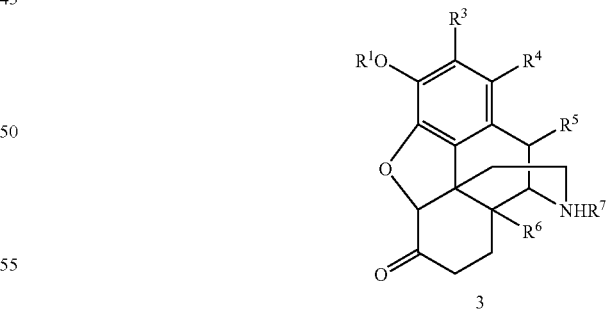

wherein:
- $R^1$ is selected from the group consisting of hydrogen, hydrocarbyl and substituted hydrocarbyl;
- $R^{1a}$ is an oxygen protecting group;
- $R^2$ is selected from the group consisting of hydrocarbyl, and substituted hydrocarbyl;
- $R^3$, $R^4$, $R^5$, and $R^6$, are independently selected from the group consisting of hydrogen, halogen, hydroxyl, {—}$OR^8$, hydrocarbyl, and substituted hydrocarbyl;

$R^7$ is selected from the group consisting of proton donors having a pKa less than about 0;
$R^8$ is selected from the group consisting of hydrocarbyl, and substituted hydrocarbyl; and
X is halogen selected from the group consisting of Cl, and Br.

An additional iteration of the invention provides a two-step process for the preparation of compound 3. The process comprises a first reaction that comprises contacting compound 1 with a proton acceptor and $XCO_2R^2$ to form compound 2. In a second reaction, compound 2 is contacted with a proton donor to form compound 3 according to the following reaction scheme:

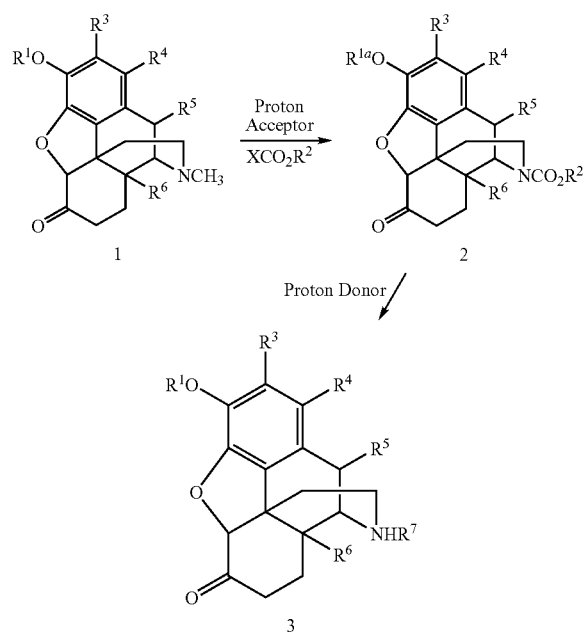

wherein:
$R^1$ is selected from the group consisting of hydrogen, hydrocarbyl and substituted hydrocarbyl;
$R^{1a}$ is an oxygen protecting group;
$R^2$ is selected from the group consisting of hydrocarbyl, and substituted hydrocarbyl;
$R^3$, $R^4$, $R^5$, and $R^6$, are independently selected from the group consisting of hydrogen, halogen, hydroxyl, {—}$OR^8$, hydrocarbyl, and substituted hydrocarbyl;
$R^7$ is selected from the group consisting of proton donors having a pKa less than about 0;
$R^8$ is selected from the group consisting of hydrocarbyl, and substituted hydrocarbyl; and
X is halogen selected from the group consisting of Cl, and Br.

Other aspects and iterations of the invention are described in more detail below.

DETAILED DESCRIPTION OF THE INVENTION

A process has been discovered for the conversion of opioid derivatives into normorphinan compounds useful for making "nal" compound analgesics and antagonists. In particular, the process may be used for the production of pure normorphinan salts from crude opioid substrates. The process encompasses a two-step reaction scheme. In Step A of the process, opioid derivatives are converted to normorphinan intermediates. Through the use of a solvent displacement system, advantageously, the normorphinan intermediates do not need to be isolated as solids throughout the entire synthetic route depicted in Reaction Scheme 1. In Step B of the process, the normorphinan intermediates are subjected to hydrolysis to produce crystalline normorphinan salts. For purposes of illustration, Reaction Scheme 1 depicts the production of compound 3 (i.e., normorphinan salt) from compound 1 (i.e., opioid derivative) in accordance with one aspect of the present invention:

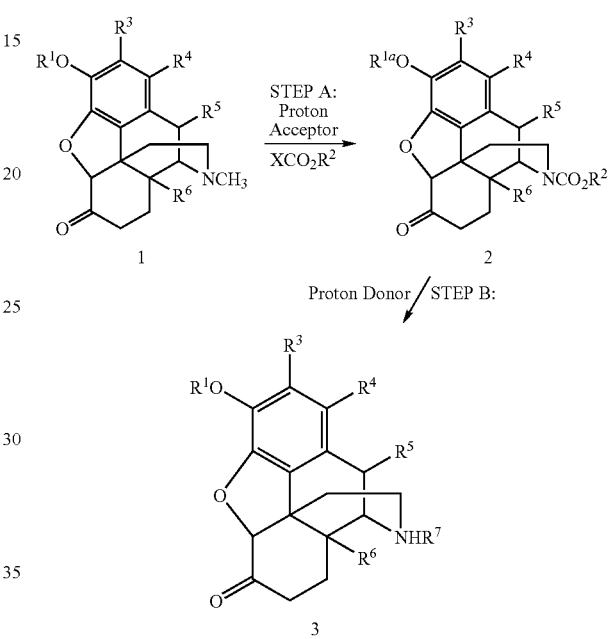

wherein:
$R^1$ is selected from the group consisting of hydrogen, hydrocarbyl and substituted hydrocarbyl;
$R^{1a}$ is an oxygen protecting group;
$R^2$ is selected from the group consisting of hydrocarbyl, and substituted hydrocarbyl;
$R^3$, $R^4$, $R^5$, and $R^6$, are independently selected from the group consisting of hydrogen, halogen, hydroxyl, methoxy, {—}$OR^8$, hydrocarbyl, and substituted hydrocarbyl;
$R^7$ is selected from the group consisting of proton donors having a pKa less than about 0;
$R^8$ is selected from the group consisting of hydrocarbyl, and substituted hydrocarbyl; and
X is halogen selected from the group consisting of Cl, and Br.

In one exemplary embodiment, the substituents of Reaction Scheme 1 comprise:
$R^1$ is selected from the group consisting of hydrogen, acyl, alkyl, alkenyl, aryl, substituted alkyl, substituted alkenyl, substituted aryl, and alkoxycarbonyl;
$R^2$ is selected from the group consisting of alkyl, alkenyl, aryl, substituted alkyl, substituted alkenyl, and substituted aryl;
$R^3$, $R^4$, $R^5$, and $R^6$ are independently selected from the group consisting of hydrogen, halogen, hydroxyl, acyl, alkyl, alkenyl, aryl, substituted alkyl, substituted alkenyl, substituted aryl, alkoxycarbonyl, carbonyl;

$R^7$ is selected from the group consisting of sulfuric acid, methanesulfonic acid, toluenesulfonic acid, phosphoric acid, hydrochloric acid, and hydrobromic acid; and X is chloride.

(I) Step A: Conversion of Compound 1 to Compound 2

Step A of the process comprises contacting an opioid derivative (compound 1) with $XCO_2R^2$ in the presence of a proton acceptor to form one or more nonmorphinan intermediates (compound 2). The reaction mixture is then quenched with a protic solvent, and side products are removed from the reaction mixture by a wash step. The reaction mixture is then subjected to a solvent displacement step.

(a) Reaction Parameters

Generally, the substrate for preparation of compound 2 corresponds to compound 1 depicted in Reaction Scheme 1. In an exemplary embodiment, compound 1 is selected from the group consisting of oxymorphone, oxycodone, hydrocodone, hydromorphone, and derivatives of each of these compounds. When compound 1 comprises oxymorphone, $R^1$ is hydrogen, $R^3$, $R^4$, and $R^5$ are each hydrogen; and $R^6$ is hydroxyl. Alternatively, when compound 1 comprises oxycodone, $R^1$ is methyl, $R^3$, $R^4$, and $R^5$ are each hydrogen; and $R^6$ is hydroxyl. When compound 1 comprises hydrocodone, $R^1$ is methyl, $R^3$, $R^4$, and $R^5$ are each hydrogen; and $R^6$ is hydrogen. Alternatively, when compound 1 comprises hydromorphone, $R^1$ is hydrogen, $R^3$, $R^4$, and $R^5$ are each hydrogen; and $R^6$ is hydrogen.

In Step A of the process, compound 1 is contacted with $XCO_2R^2$. Exemplary hydrocarbyl or substituted hydrocarbyl groups comprising $R^2$ include alkyl, alkenyl, aryl, substituted alkyl, substituted alkenyl, and substituted aryl. Included among some of the more preferred hydrocarbyl or substituted hydrocarbyl groups comprising $R^2$ are methyl, ethyl, propyl, isopropyl, butyl, isobutyl, tertiary butyl, pentyl, cyclopropyl, cyclobutyl, cyclopentyl, cyclohexyl, phenyl, methylphenyl, or benzyl. For each of the foregoing embodiments, X may be chloride or bromide. In an exemplary embodiment, X is chloride, and $R_2$ is ethyl.

Step A of the process is typically carried out in the presence of a proton acceptor. In general, the proton acceptor has a pKa of between about 7 and about 13, preferably between about 8 and about 10. Representative proton acceptors that may be employed include, but are not limited to, borate salts (such as, for example, $NaBO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic proton acceptors (such as, for example, pyridine, triethylamine, diisopropylethylamine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl)piperazine-1-ethanesulfonic acid (HEPES), 2-(4-morpholinyl) ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. In one embodiment, the proton acceptor is selected from the group consisting of $NaHCO_3$, $KHCO_3$, $LiHCO_3$, $KHCO_3$, $LiHCO_3$, $K_2CO_3$, NaOH, KOH, $Na_2HPO4Na_3PO_4$, $K_2HPO_4/K_3PO_4$, and mixtures thereof. In a preferred embodiment, the proton acceptor is $NaHCO_3$, $KHCO_3$, or a combination thereof.

The amount of reactants used in Step A of the process can and will vary without departing from the scope of the invention. In general, the molar ratio of compound 1 to $XCO_2R^2$ to proton acceptor is from about 1:2:1 to about 1:20:20. More typically, the molar ratio of compound 1 to $XCO_2R^2$ to proton acceptor is from about 1:6:3 to about 1:12:5.

Step A of the process is also typically conducted in the presence of an aprotic solvent. The proton acceptor, and $XCO_2R^2$ reagent are preferably selected to increase the solubility of compound 1 and/or compound 2 in the aprotic solvent. Non-limiting examples of aprotic solvents include ether solvents, acetonitrile, benzene, dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), N,N-dimethylacetamide (DMAC), N-methylpyrrolidinone (NMP), ethyl acetate, ethyl formate, ethyl-methyl ketone, isobutylmethylketone, formamide, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), toluene, trichloromethane. Preferred aprotic solvent may comprise chloroform, 1,2-dichloroethane, toluene, chlorobenzene, ethyl acetate, propyl acetate, isopropyl acetate, THF, acetonitrile, and mixtures thereof. In an exemplary embodiment, the aprotic solvent is chloroform. Typically, the amount of aprotic solvent to compound 1 is about 2:1 (g/g).

To form the reaction mixture, compound 1 is typically combined with the solvent(s) prior to the addition of $XCO_2R^2$ and the proton acceptor. Alternatively, however, the solvent(s), $XCO_2R^2$, and the proton acceptor may be combined and thereafter added to the reaction vessel containing compound 1.

The temperature of the reaction mixture for Step A of the process will typically be within the range of about 50° C. to about 80° C. More typically, the reaction will be carried out at a temperature between about 55° C. and about 65° C. The reaction may also be performed under ambient pressure or in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of the reactants, and a significantly increased amount of product compared to the amounts of each present at the beginning of the reaction. In general, the reaction proceeds for about 1 hour to about 48 hours, and more typically, for about 9 hours to about 15 hours.

After the reaction is completed, the reaction mixture is typically quenched in a protic solvent. An exemplary protic solvent is water. The reaction mixture, at this point, generally separates into two layers: an organic layer, and an aqueous layer.

(b) Removal of Side Products and Remaining Starting Materials

As will be appreciated by a skilled artisan, one or more unwanted side products are typically produced in Step A. In this context, the term "unwanted side product" includes compounds not comprising formula 2. The side products can and will vary depending upon the chemical composition of the substrate (i.e., compound 1), and other reactants. By way of example, when compound 1 comprises oxymorphone, the major side products may include 3-O-ethocycarbonylxoymorphone and 3-O-, 14-O-diethoxycarbonyl oxymorphone and mixtures thereof. Alternatively, when compound 1 comprises oxycodone, the major side products may include 14-O-ethoxycarbonyl oxycodone. Alternatively, when compound 1 comprises hydromorphone, the major side products may include 3-O-ethoxycarbonyl hydromorphone.

To increase final product yield and purity of compound 2, and ultimately, of compound 3, the side products are generally substantially removed from the reaction mixture. In an exemplary embodiment, the side products may be removed from the reaction mixture by a wash step. The wash step generally comprises contacting the organic layer (described above in (Ia)) of the reaction mixture with an acidic protic solvent that has a pH below 7. In an exemplary embodiment, the acidic protic solvent will be acidic water having a pH ranging from about 0.1 to about 2.0. After the organic layer is washed with the acidic protic solvent, the aqueous layer, which contains a substantial amount of the side products, may be physically removed and discarded. The wash step may be repeated from about 2 to about 10 times, and more preferably, from about 3 to about 6 times.

Typically, the side products remaining in the organic layer after the wash step(s) comprises from about 0.01% to about 2% area/area of the organic layer, and in an exemplary embodiment, the side products remaining in the organic layer may comprise less than about 0.5% area/area of the organic layer. In general, the amount of compound 2 remaining in the organic layer after the wash step(s) comprises from about 80% to about 99% area/area of the organic layer. In exemplary embodiments, the amount of compound 2 remaining in the organic layer after the wash step(s) is at least 90%, at least 95%, at least 97%, or greater than 99% area/area of the organic layer.

(c) Solvent Displacement

The reaction mixture may be subjected to a solvent displacement process that is applied to displace one solvent for another. In this context, a second solvent may be added to the reaction mixture, and the solvent present in the reaction mixture may be removed via solvent displacement methods (e.g. distillation, direct displacement, or salting out). Through the use of this solvent displacement process, the normorphinan intermediates (i.e., compound 2) do not need to be isolated as solids throughout the entire synthetic route depicted in Reaction Scheme 1. While it is possible to conduct solvent displacement on the reaction mixture at the end of the process detailed in (Ia), in an exemplary embodiment, the reaction mixture is subjected to the wash procedure detailed in (Ib) prior to solvent displacement.

In general, solvent displacement may be applied to the reaction mixture to decrease or replace the aprotic solvent utilized in (Ia) (referred to in this paragraph as the "first solvent") with a second solvent. In an exemplary embodiment, the solvent displacement method is distillation, and is preferably, vacuum distillation. The second solvent typically will have a higher boiling point compared to the first solvent. Because the second solvent has a higher boiling point than the first solvent, the first solvent may be displaced by distillation. Suitable second solvents include alcohols having from 3 to 8 carbon atoms, and proton donors having from 2 to 8 carbon atoms. An exemplary solvent pair, for example, may comprise chloroform as the first solvent, and propionic acid as the second solvent. In an exemplary embodiment, vacuum distillation is conducted at a temperature of about 85° C. The distillation process preferably does not require distillation to dryness, and as such, generally no solids are formed.

(II) Step B: Hydrolysis of Compound 2 to Form Compound 3

In Step B of the process, compound 2 is subjected to hydrolysis to form compound 3. Compound 3 is a normorphinan salt. In an exemplary embodiment, the normorphinan salt is selected from the group consisting of a noroxymorphone salt, a noroxycodone salt, a norhydrocodone salt, and a norhydromorphone salt.

The hydrolysis reagents, in an exemplary embodiment of Step B, are selected so that they substantially dissolve all of the reactants at the initial stages of the hydrolysis reaction. In this context, preferably at least about 90% of the reactants are dissolved within 3 hours after the start of the hydrolysis reaction. Because substantially all of the hydrolysis reactants are dissolved at the beginning of the hydrolysis reaction, the reaction rate is maximized, and cross contamination of the product (i.e., compound 3) with starting reagents is significantly diminished.

The hydrolysis reaction of Step B involves contacting compound 2 with a proton donor in the presence of a solvent system. The proton donor typically will have a pKa of less than 0. Suitable proton having this characteristic include, but are not limited to $MeSO_3H$, poly $H_3PO_4$, $H_3PO_4$, $H_2SO_4$, HCl, HBr, $HClO_4$, HI, $HNO_3$, $CF_3SO_3H$, p-methyltoluenesulfonic acid, $HClO_3$, $HBrO_4$, $HIO_3$, and $HIO_4$.

The molar ratio of compound 2 to proton donor may range from about 1:1.5 to about 1:10. More typically, the molar ratio of compound 2 to proton donor may range from about 1:3 to about 1:5.

Because the process depicted in Reaction Scheme 1 is conducted in a continuous manner (i.e., the hydrolysis reaction is typically conducted after the solvent displacement process of (Ic)), the solvent system utilized in the hydrolysis reaction will typically include the solvent(s) remaining after distillation. In this context, the solvent system will typically comprise an amount of protic solvent remaining after distillation. In an exemplary embodiment, the protic solvent will comprise propionic acid. The solvent system may alternatively, or additionally, comprise other protic solvents such as alcohol or other water-miscible solvent; thus, for example, the protic solvent phase may be water, a water/alcohol mixture, or a water/water-miscible solvent mixture. Representative alcohols for the water/alcohol mixture include, for example, methanol, ethanol, isopropyl alcohol, isobutyl alcohol, t-butyl alcohol, n-propyl alcohol, n-butyl alcohol, and combinations thereof. Other water-miscible solvents for the water/water-miscible solvent mixture include, for example, acetonitrile, N,N-dimethylformamide, 1-methyl-2-pyrrolidinone, N,N-dimethylacetamide, acetone, tetrahydrofuran, acetic acid, propionic acid, hexanoic acid, and combinations thereof. In an exemplary embodiment, the solvent system will comprise propionic acid, and water, and the proton donor will comprise $MeSO_3H$.

Optionally, an antioxidant compound may also be added to the hydrolysis reaction in order to improve the purity of compound 3. Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (paba), butylated hydroxyanisole (bha), butylated hydroxytoluene (bht), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, n,n'-diphenyl-p-phenylenediamine (dppd), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (edta), eucalyptus extract, eugenol, ferulic acid, flavonoids (e.g., catechin, epicatechin, epicatechin gallate, epigallocatechin (egc), epigallocatechin gallate (egcg), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; r-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (ndga), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., ionox 100), 2,4-(tris-3',5'-bi-tert-butyl-4'-hydroxybenzyl)-mesitylene (i.e., ionox 330), 2,4,5-trihydroxybutyrophenone, ubiquinone, tertiary butyl hydroquinone (tbhq), thiodipropionic acid, trihydroxy butyrophenone, tryptamine, tyramine, uric acid, vitamin k and derivates, vitamin q10, wheat germ oil, zeaxanthin, or combinations thereof. The amount of antioxidant may range from about 0.002 to about 0.02 by weight of the reaction mixture.

The reaction may be conducted at a temperature ranging from about 75° C. to about 150° C. More preferably, the reaction may be conducted at a temperature ranging from about 90° C. to about 115° C. In another embodiment, the reaction may be conducted at a temperature ranging from about 95° C. to about 110° C. The reaction is preferably performed under ambient pressure, and preferably in an inert atmosphere (e.g., nitrogen or argon).

After hydrolysis, compound 3 is generally formed as a crystalline compound that may be isolated from the reaction mixture by methods known in the art such as by filtration and/or centrifugation. The purity of compound 3 is typically at least 90% as determined by chromatography (e.g., HPLC). In exemplary embodiments, the purity of compound 3 is at least 95%, at least 96%, at least 97%, at least 98%, at least 99%, or greater than 99.5% as determined by chromatography. The overall yield of compound 3 prepared from compound 1 may range from about 65% to about 85% (mol/mol).

The process described herein may be used to produce compounds, i.e., compounds 2 or 3, that have either a (−) or (+) stereochemistry configuration, with respect to the rotation of polarized light. More specifically, each chiral center may have an R or an S configuration. For ease of discussion, the ring atoms of the core morphinan structure referenced herein are numbered as follows:

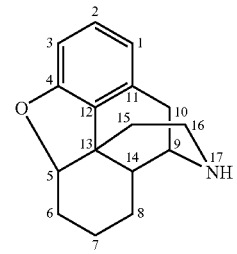

As illustrated in the core morphinan structure, there are four chiral carbons comprising any of the compounds utilized in the process of the invention (i.e., compound 1, 2, or 3), i.e., carbons 5, 13, 14, and 9. Thus, the configuration of compounds 1, 2, or 3 may be RRRS, SRRS, SRSS, RSRR, RSSR, SSRR, or SSSR with respect to C5, to C13, C14, and C9.

(III) Compounds Prepared from Compound 3

Compounds corresponding to compound 3 may be end products themselves, or intermediates that may be further derivatized in one or more steps to yield further morphinan intermediates or end products. By way of non-limiting example, one or more compounds corresponding to compound 3 may be used in processes to produce a compound selected from the group consisting of nalbuphine, nalmefene, naloxone, naltrexone, naltrexone methobromide, 3-O-methyl naltrexone, naltrexol, naloxol, and the salts, intermediates, and analogs thereof. General reaction schemes for the preparation of such commercially valuable morphinans are disclosed, among other places, in U.S. Pat. No. 4,368,326 to Rice, the entire disclosure of which is hereby incorporated by reference herein.

Additionally, in some embodiments, N-alkylation of compound 3 may be used to form the N-hydrocarbyl derivative of compound 3 in which the 6-ketone can be reduced to 6-α-OH, 6-β-OH, 6-α-NH$_2$, or 6-β-NH$_2$.

DEFINITIONS

The term "acyl," as used herein alone or as part of another group, denotes the moiety formed by removal of the hydroxy group from the group COOH of an organic carboxylic acid, e.g., RC(O)—, wherein R is R$_1$, R$_1$O—, R$_1$R$_2$N—, or R$_1$S—, R$_1$ is hydrocarbyl, heterosubstituted hydrocarbyl, or heterocyclo, and R$_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkaryl" or "alkylaryl" as used herein describes groups which are preferably aryl groups having a lower alkyl substituent, such as toluyl, ethylphenyl, or methylnapthyl.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aralkyl" as used herein describes groups which are preferably lower alkyl containing from one to eight carbon atoms having an aryl substituent, such as benzyl, phenylethyl, or 2-napthylmethyl.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "charged" as used herein describes adding compound or reagents to a vessel.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

The terms "hydroxyl protecting group" as used herein denote a group capable of protecting a free hydroxyl group ("protected hydroxyl"), which, subsequent to the reaction for which protection is employed, may be removed without disturbing the remainder of the molecule.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples describe various iterations of the invention.

The following examples detail the synthesis of pure noroxymorphone salts from crude oxymorphone. The reaction scheme is presented below:

For laboratory scale synthesis, the reaction vessels (reactors) were three-neck flasks

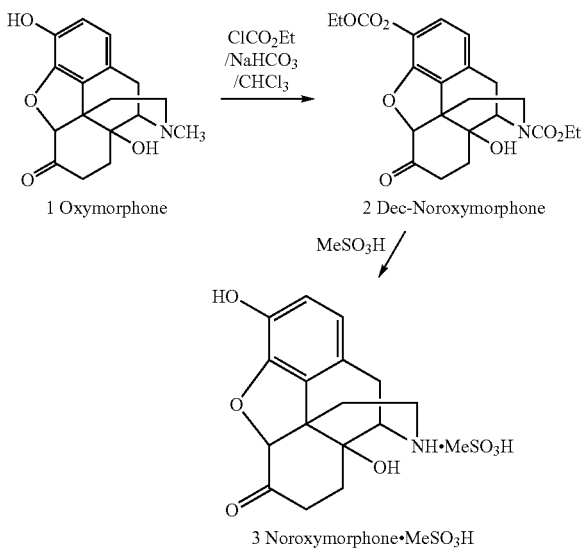

(i.e., 1.0 L flasks for a scale of 0.10 kg of oxymorphone charged). Each vessel was equipped with an agitator, a cooling condenser, a nitrogen inlet, and an outlet, as well as an addition funnel.

Example 1

Initial Prototype Preparation of Noroxymorphone Salts from Crude Oxymorphone Crude oxymorphone (actual weight of pure oxymorphone was determined by multiplying the weight of the crude oxymorphone by its wt/wt %) and chloroform ($CHCl_3$) (3.36 kg per kg of oxymorphone charged) were added to a reactor. The agitator was turned on to stir the reactant mixture and the reactor was flushed with nitrogen. Then sodium bicarbonate ($NaHCO_3$) (1.4 kg per kg of oxymorphone charged) and ethyl chloroformate (EtOCOCl) (3.74 kg per kg of oxymorphone charged) were added to the reactor. The reactor was heated at a rate of about 0.5° C. per minute until a temperature of 64±2° C. was reached, and then this temperature was maintained for a minimum of 9 hours. The progress of the reaction was monitored by HPLC analysis. The reaction products included dec-noroxymorphone (3-O-, 17-N-diethoxycarbonylnoroxymorphone) and tec-noroxymorphone (3-O-, 14-O-, 17-N-triethoxycarbonylnoroxymorphone).

Upon completion of the reaction, the mixture was cooled to a temperature of less than 30° C. To remove the side products and the remaining starting materials from the reaction (i.e., EtOCO-derivatives of oxymorphone and oxymorphone), the chloroform-containing reaction product was washed with acidic water. For this stage, water (3.6 L per kg of oxymorphone charged) was added to the reactor, and the mixture was stirred for about 30-45 minutes. The pH of the mixture was adjusted to a value of about 0.8-2.0 by adding either 70% methane sulfonic acid ($MeSO_3H$) or 50% NaOH as necessary. The agitator was turned off and the mixture was allowed to settle into two phases. The lower, chloroform phase was transferred to a new reactor, and the upper, aqueous phase was discarded. With the agitator running, water (2.0 L per kg of oxymorphone charged) was added to the chloroform phase in the new reactor, and 70% $MeSO_3H$ or 50% NaOH was added until the pH of the mixture reached about 0.8-2.0. The agitator was stopped, the mixture was allowed to form two phases, and the lower, chloroform phase was transferred to another reactor. The organic phase was washed with acidic water one more time, essentially as described above, and transferred to another reactor.

With the agitator on, propionic acid (EtCOOH) (0.75 L per kg of oxymorphone charged) was added to the reactor containing the washed chloroform phase. Distillation equipment was assembled, a vacuum was applied to the reactor, and the temperature of the reaction mixture was raised to about 80-85° C. to distill off the solvents. Once the total volume of the residue was about 1.8 L (i.e., about 1.6-2.0 L per kg of oxymorphone charged), the vacuum line was turned off and the reactor was refilled with nitrogen.

To the remaining mixture in the reactor, EtCOOH (1.0 L per kg of oxymorphone charged), water (0.7 L per kg of oxymorphone charged), 6% sulfurous acid ($H_2SO_3$, 2.0 L per kg of oxymorphone charged), and 70% $MeSO_3H$ (2.0 L per kg of oxymorphone charged) were added. The mixture was heated to about 107±3° C. to distill off some of the volatilized solvents, and the reaction mixture was maintained at this temperature for about 9-12 hours. The hydrolysis reaction was monitored by HPLC. The total mass of solvents distilled off was about 0.5-1.0 L per kg of oxymorphone charged, and crystals appeared in the mixture after 3-4 hours of heating.

Upon completion of the hydrolysis reaction, the reaction mixture was cooled to less than 35° C., and 3.0 L of isopropanol (IPA) was added. The mixture was then cooled to about 5-10° C. and held at that temperature for 1-2 hours. The resulting suspension in the reactor was filtered through a glass filter. In addition, the reactor was rinsed with a cold (5-10° C.) solution of 96% $MeSO_3H$:H2O:IPA (3:7:30 volume ratio) (0.5 L per kg of oxymorphone charged), and the rinse was transferred to the glass filter. The reactor was rinsed again with a solution of 96% $MeSO_3H$:H2O:IPA as described above and this rinse was also transferred to the glass filter. The solids on the filter were rinsed with IPA (0.5 L per kg of oxymorphone charged) and then dried by pulling air through the solids into a vacuum line at room temperature for 20 hour. The yield of noroxymorphone.$MeSO_3H$ was 70-80% mol/mol (~1.0 kg per kg of oxymorphone charged). The solids were further dried under a vacuum at 80° C. for 20 hours if not completely dried.

Example 2

Preparation of Noroxymorphone Salts

Trial 2

Crude oxymorphone, containing 200 g of oxymorphone, and 460 g of $CHCl_3$ were added to a reactor. The agitator was turned on and the vessel was flushed with nitrogen. To the reactor, 232 g of $NaHCO_3$ was added, and then 748 g of EtOCOCl was gradually added to the reactor over a period of 15 minutes while maintaining the reaction mixture at a temperature of less than 55° C. After all of the EtOCOCl was added to the reactor, the reaction mixture was stirred for an additional 30 minutes. The reaction mixture was then heated to a temperature of about 60-65° C., and maintained at that temperature range for 9 hours, then cooled to a temperature of less than 35° C. upon completion of the reaction.

The cooled mixture was transferred to a second reactor in which 400 mL of water was added with the agitator running. The original reactor was washed with 200 mL of water, and this water, containing residual reaction mixture, was also added to the second reactor, and the entire mixture was stirred in the reactor for 30-45 additional minutes. Once all solids were dissolved, the agitator was stopped, and the reaction mixture was allowed to settle into two phases. The lower chloroform phase was transferred back to the original reactor, the agitator was started, and the upper aqueous phase in the second reactor was discarded. While stirring, 300 mL of water was added to the reaction mixture, followed by 70% $MeSO_3H$ until the pH of the reaction mixture fell below a value of 1. An additional 100 mL of water was added to the reactor, the mixture was stirred for an additional 15 minutes, and then the agitator was stopped, allowing the mixture to settle into two phases. The lower chloroform phase was transferred back to the second reactor and the agitator was started, and the upper aqueous phase was discarded.

While stirring the mixture in the second reactor, 400 mL of water was added, followed by a sufficient amount of 70% $MeSO_3H$ (approximately 4 g of $MeSO_3H$) to lower the pH of the mixture to a value of less than 1. The agitator was then turned off and the mixture was allowed to settle into two phases. The lower chloroform phase was transferred back to the original reactor, and the upper aqueous phase was discarded.

With the agitator on, 100 mL of propionic acid (EtCOOH) was added to the reactor containing the washed chloroform phase. Distillation equipment was assembled, a vacuum of 100 mm Hg was applied, and the temperature of the mixture was raised to about 50° C. to distill off the solvents. After the mixture had achieved a temperature of about 50° C., the vacuum was held at a value of less than 150 mm, and the temperature of the mixture was raised to about 85° C. After holding these conditions for one hour, the vacuum was removed from the reactor.

To the reactor, 200 mL of EtCOOH, 300 mL of water, 6.6 mL of 6% $H_2SO_3$, and 150 mL of 99.5% $MeSO_3H$ were added. The mixture was heated to 107±1° C. and maintained at this temperature for 12 hours to distill off about 80-100 mL of the volatilized solvents. The reaction mixture was then cooled to a temperature of about 0-5° C.

As soon as the temperature of the reaction mixture fell below 25° C., 600 mL of IPA was added. When the reaction mixture had achieved a temperature of about 0-5° C., this temperature was held for about 2 hours. The resulting suspension was filtered through a glass filter, and the suspension resulting from rinsing the reactor three times with 100 mL of a $MeSO_3H:H_2O:IPA$ solution (3:7:30 volume ratio) that was pre-chilled to a temperature of about 5-10° C. The filtered solids were dried in vacuum for 18 hours at a temperature of about 50-60° C., resulting in the formation of white crystals. The yield of the product for this experiment was about 75%.

Example 3

Preparation of Noroxymorphone Salts

Trial 3

A reactor was loaded with crude oxymorphone, containing 30 g of oxymorphone, and 69.1 g of $CHCl_3$. The agitator was turned on and the vessel was flushed with nitrogen. To the reactor, 35 g of $NaHCO_3$ was added, and then 112.6 g of EtOCOCl was gradually added to the reactor over a period of 15 minutes while maintaining the reaction mixture at a temperature of less than 55° C. After all of the ethyl chloroformate was added to the reactor, the reaction mixture was stirred for an additional 30 minutes. The reaction mixture was then heated to a temperature of about 60-65° C., and maintained at that temperature range for 9 hours. Upon completion of the reaction, the mixture was cooled to a temperature of less than 35° C.

The cooled mixture was transferred to a second reactor in which 60 mL of water was stirring. The original reactor was washed with 60 mL of water, and this water, containing residual reaction mixture, was also added to the second reactor, and the entire mixture was stirred for 30-45 additional minutes. Once all solids were dissolved, the agitator was stopped, and the reaction mixture was allowed to settle into two phases. The lower chloroform phase was transferred back to the original reactor, the agitator was started, and the upper aqueous phase from the second reactor was discarded. While stirring, 60 mL of water was added to the reaction mixture, followed by 70% $MeSO_3H$ until the pH of the reaction mixture fell below a value of 1. The agitator was then stopped, allowing the mixture to settle into two phases. The lower, chloroform phase was transferred back to the original reactor and the agitator was started, and the upper aqueous phase was discarded.

To the stirring mixture in the reactor, 60 mL of water was added, followed by a sufficient amount of 70% $MeSO_3H$ to lower the pH of the mixture to a value of less than 1. The agitator was then turned off and the mixture was allowed to settle into two phases. The lower chloroform phase, containing diethoxycarbony-noroxymorphone and triethoxycarbony-noroxymorphone, was transferred into another reactor, and the upper aqueous phase was discarded.

To the chloroform phase in the reactor, 30 mL of IPA, 15 ml of water, and then 30 g of $MeSO_3H$ was added, and the resulting mixture was then heated to a temperature of about 90° C. to distill off the $CHCl_3$. The mixture was subsequently heated to a temperature of about 95-100° C. and held at this temperature for over one hour. To the mixture, 9 mL of water were added, followed by heating to a temperature of about 95-105° C. for 6 hours to distill off more solvent. An additional 9 mL of water was added to the mixture, followed by an additional 6 hours at 95-105° C. to distill off additional solvent. After cooling the mixture to 75° C., 15 mL of water and 5 mL of IPA were added, then the mixture was cooled to room temperature for one hour. The resulting suspension was filtered, and the filtered solids were washed twice with 15 mL of a 1:2 aqueous solution of $MeSO_3H/H_2O$ and then washed four times with 15 mL of acetone. The resulting solid was dried at a temperature of 55° C. under vacuum conditions for 2 days, yielding 30.6 g of solid product.

Example 4

Preparation of Noroxymorphone Salts

Trial 3

A chloroform phase containing diethoxycarbonyl-noroxymorphone and triethoxycarbony-noroxymorphone, prepared using the protocol described in Example 3, was transferred to a reactor. To the mixture, 30 mL of t-butyl alcohol (t-BuOH), 15 mL of water, and then 21 g of $MeSO_3H$ were added. The solution, which started at a temperature of less than 35° C., was heated to a temperature of about 90° C. to distill off the chloroform ($CHCl_3$). The mixture was subsequently heated to a temperature of about 95-100° C. and held at this temperature for over one hour. To the mixture, 6 mL of water were added, followed by heating to a temperature of about 95-105° C. for 6 hours. An additional 15 mL of water was added to the mixture, followed by an additional 6 hours at 95-105° C. After cooling the mixture to 75° C., 15 mL of water and 5 mL of IPA were added, then the mixture was cooled to room temperature for one hour. The resulting suspension was filtered, and the filtered solids were washed twice with 15 mL of a 1:2 aqueous solution of $MeSO_3H/H_2O$ and then washed four times with 15 mL of acetone. The resulting solid was dried at a temperature of 55° C. under vacuum conditions for 2 days, yielding 30.6 g of solid product.

Example 5

Preparation of Noroxymorphone Salts

Trial 4

A chloroform phase containing diethoxycarbonyl-noroxymorphone and triethoxycarbony-noroxymorphone was prepared using the protocol described in Example 3, transferred to a reactor, and pumped down to dryness, yielding a sticky solid. To the sticky solid, 10 mL of hexanoic acid and 50 mL of water were added, followed by the gradual addition of 20 mL of concentrated sulfuric acid (c-$H_2SO_4$). The reaction mixture was then heated to a temperature of 105° C., and maintained for two hours at this temperature. The mixture was then cooled to 10° C. for two hours, and the resulting suspension was filtered. The filtered solids were washed twice with 15 mL of a 1:2 aqueous solution of $MeSO_3H/H_2O$ and then washed four times with 15 mL of acetone. The resulting solid was dried at a temperature of 55° C. under vacuum conditions for 2 days, yielding 24.3 g of solid product.

Example 6

Improved Preparation of Noroxymorphone Salts

Trial 5—with Higher Yield

A reactor was charged with crude oxymorphone, containing 31 g of oxymorphone, and 46 g of $CHCl_3$. The agitator was turned on and the vessel was flushed with nitrogen. To the reactor, 46 g of $NaHCO_3$ was added, and then 75 g of ethyl chloroformate was gradually added to the reactor over a period of 15 minutes while maintaining the reaction mixture at a temperature of less than 55° C. After all of the ethyl chloroformate was added to the reactor, the reaction mixture was stirred for an additional 30 minutes. The reaction mixture was then heated to a temperature of about 60-65° C., and maintained at that temperature range for 9 hours. Upon completion of the reaction, the mixture was cooled to a temperature of less than 35° C.

The cooled mixture was transferred to a second reactor in which 40 mL of water was stirring. The original reactor was washed with 40 mL of water, and this water, containing residual reaction mixture, was also added to the second reactor, and the entire mixture was stirred for an additional 30-45 minutes. Once all solids in the mixture were dissolved, the agitator was stopped, and the reaction mixture was allowed to settle into two phases. The lower chloroform phase was transferred back to the original reactor, the agitator was started, and the upper aqueous phase in the second reactor was discarded. While stirring, 40 mL of water was added to the reaction mixture followed by sufficient 70% $MeSO_3H$ to lower the pH of the reaction mixture to a value below 1. The agitator was again stopped, allowing the mixture to settle into two phases. The lower chloroform phase was transferred back to the second reactor and the agitator was started, and the upper aqueous phase was discarded. The process of adding 40 mL of water and $MeSO_3H$ to lower the pH of the mixture to a value less than 1, followed by the removal of the lower chloroform phase was repeated. The chloroform phase was transferred back to the original reactor, and the agitator was restarted.

With the agitator on, 10 mL of propionic acid (EtCOOH) was added to the reactor containing the washed chloroform phase. Distillation equipment was assembled, a vacuum of 100 mm Hg was applied, and the temperature of the reaction mixture was raised to about 50° C. After reaching 50° C., vacuum was applied at less than 150 mm Hg for 15 minutes, while increasing the temperature of the mixture to 85° C. After the mixture had reached a temperature of 85° C., the mixture was maintained at this temperature under a vacuum of 120 mm Hg.

The distillation equipment, including the vacuum, was removed, and 20 mL of EtCOOH, 30 mL of water, 6.8 g of $H_2SO_3$, and 15 mL of 99.5% $MeSO_3H$ was added to the mixture. The mixture was heated to 107±1° C. and held at this temperature for 12 hours to distill off the solvents. The mixture was then cooled to temperature of 0-5° C. When the mixture had reached a temperature of less than 25° C., 60 mL of IPA was added, and the mixture was maintained at a temperature of 0-5° C. for two additional hours.

The resulting suspension was then filtered through a glass filter, and the suspension resulting from rinsing the reactor three times with 10 mL of $MeSO_3H/H_2O/IPA$ in a volume ratio of 3:7:30, pre-cooled to a temperature of 5-10° C. was also filtered through the glass filter. The filtered solids were dried under vacuum conditions at a temperature of 50-60° C. for twenty hours to give white crystals. The yield of noroxymorphone.MeSO3H was 82%.

What is claimed is:

1. A process for the preparation of compound 2 from compound 1 according to the following reaction:

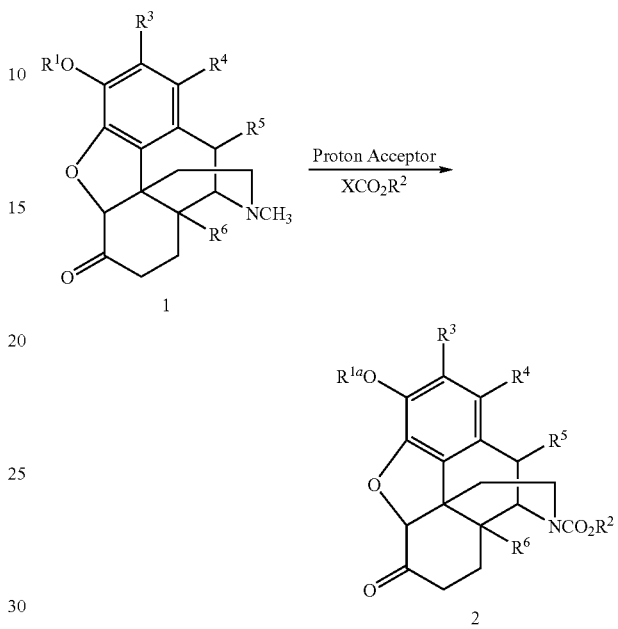

wherein:
$R^1$ is selected from the group consisting of hydrogen, hydrocarbyl and substituted hydrocarbyl;
$R^{1a}$ is an oxygen protecting group;
$R^2$ is selected from the group consisting of alkyl and aryl;
$R^3$, $R^4$ and $R^5$, are independently selected from the group consisting of hydrogen, halogen, hydroxyl, methoxy, {—}$OR^8$, hydrocarbyl, and substituted hydrocarbyl;
$R^6$ is selected from the group consisting of hydrogen, halogen, hydroxyl and hydrocarbyl;
$R^8$ is selected from the group consisting of hydrocarbyl, and substituted hydrocarbyl; and
X is halogen selected from the group consisting of Cl, and Br.

2. The process of claim 1, wherein:
$R^1$ is selected from the group consisting of hydrogen, acyl, alkyl, alkenyl, aryl, substituted alkyl, substituted alkenyl, substituted aryl, and alkoxycarbonyl;
$R^2$ is alkyl;
$R^3$, $R^4$ and $R^5$, are independently selected from the group consisting of hydrogen, halogen, hydroxyl, acyl, alkyl, alkenyl, aryl, substituted alkyl, substituted alkenyl, substituted aryl, alkoxycarbonyl, and carbonyl;
$R^6$ is selected from the group consisting of hydrogen, halogen, hydroxyl, alkyl and aryl; and
X is chloride.

3. The process of claim 1, wherein the proton acceptor has a pKa of greater than about 7; the reaction is conduced in the presence of an aprotic solvent; the molar ratio of compound 1 to $XCO_2R^2$ to proton acceptor is from about 1:3:1 to about 1:20:20, and the reaction is conducted at a temperature ranging from about 50° C. to about 80° C.

4. The process of claim 1, wherein compound 2 comprises a mixture of compounds selected from the group consisting of noroxymorphone derivatives and noroxycodone derivatives.

5. The process of claim 1, wherein the process results in the formation of side product compounds not having formula 2, and the reaction mixture separates into an organic layer, and an aqueous layer after the reaction mixture is quenched with a protic solvent.

6. The process of claim 5, wherein the side product compounds and compounds having formula 1 are removed from the reaction mixture by a wash step, the wash step comprising contacting the organic layer with a protic solvent having a pH from about 0.8 to about 2.0, followed by separation of the aqueous layer from the reaction mixture.

7. The process of claim 6, wherein the amount of compound 1 and side product compounds remaining in the organic layer after the wash step comprises from about 0.01% to about 2% area/area of the organic layer; and the amount of compound 2 remaining in the organic layer after the wash step comprises from about 80% to about 99% area/area of the organic layer.

8. The process of claim 6, wherein the aprotic solvent is displaced with a second solvent selected from the group consisting of an alcohol having from 3 to 8 carbon atoms, and a proton donor having from 2 to 8 carbon atoms.

9. A process for the preparation of compound 3 from compound 2 according to the following reaction:

[Chemical structure of compound 2 with substituents $R^{1a}O$, $R^3$, $R^4$, $R^5$, $R^6$, $NCO_2R^2$ → Proton Donor → Chemical structure of compound 3 with substituents $R^1O$, $R^3$, $R^4$, $R^5$, $R^6$, $NHR^7$]

wherein:
$R^1$ is selected from the group consisting of hydrogen, hydrocarbyl and substituted hydrocarbyl;
$R^{1a}$ is an oxygen protecting group;
$R^2$ is selected from the group consisting of alkyl and aryl;
$R^3$, $R^4$ and $R^5$, are independently selected from the group consisting of hydrogen, halogen, hydroxyl, {—}$OR^8$, hydrocarbyl, and substituted hydrocarbyl;
$R^6$ is selected from the group consisting of hydrogen, halogen, hydroxyl and hydrocarbyl;
$R^7$ is selected from the group consisting of proton donors having a pKa less than about 0;
$R^8$ is selected from the group consisting of hydrocarbyl, and substituted hydrocarbyl.

10. The process of claim 9, wherein:
$R^1$ is selected from the group consisting of hydrogen, acyl, alkyl, alkenyl, aryl, substituted alkyl, substituted alkenyl, substituted aryl, and alkoxycarbonyl;
$R^2$ is alkyl;
$R^3$, $R^4$ and $R^5$, are independently selected from the group consisting of hydrogen, halogen, hydroxyl, acyl, alkyl, alkenyl, aryl, substituted alkyl, substituted alkenyl, substituted aryl, alkoxycarbonyl, carbonyl;
$R^6$ is selected from the group consisting of hydrogen, halogen, hydroxyl, alkyl and aryl;
$R^7$ is selected from the group consisting of sulfuric acid, methanesulfonic acid, toluenesulfonic acid, phosphoric acid, hydrochloric acid, and hydrobromic acid.

11. The process of claim 9, wherein the proton donor has a pKa less than 0.

12. The process of claim 9, wherein the proton donor is selected from the group consisting of sulfuric acid, methanesulfonic acid, toluenesulfonic acid, phosphoric acid, hydrochloric acid, and hydrobromic acid;
the reaction is conducted in the presence of at least one protic solvent, the amount of protic solvent to compound 2 is about 2:1 (g/g), the molar ratio of compound 2 to proton donor is from about 1:1.5 to about 1:10 (g/g), and the reaction is conducted at a temperature ranging from about 90° C. to about 115° C.

13. The process of claim 9, wherein the reactants comprise compound 2, a proton donor, a protic solvent, and a second proton donor having from 2 to 8 carbon atoms.

14. The process of claim 13, wherein compound 2 comprises a mixture of noroxymorphone derivatives, the proton donor is methanesulfonic acid, the protic solvent is water, the second proton donor is propionic acid; and compound 3 is noroxymorphone.MeSO$_3$H.

15. The process of claim 13, wherein compound 2 comprises a mixture of noroxycodone derivatives, the proton donor is methanesulfonic acid, the protic solvent is water, the second proton donor is propionic acid; and compound 3 is noroxycodone methanesulfonate.

16. The process of claim 9, wherein compound 3 is formed as a crystal; the yield of compound 3 is from about 65% to about 85% (mol/mol); and the purity of compound 3 is at least 95% as determined by chromatography.

17. A process for the preparation of compound 3, the process comprising a first reaction that comprises contacting compound 1 with a proton acceptor and $XCO_2R^2$ to form compound 2, and a second reaction that comprises contacting compound 2 with a proton donor to form compound 3 according to the following reaction scheme:

[Chemical reaction scheme: compound 1 (with $R^1O$, $R^3$, $R^4$, $R^5$, $R^6$, $NCH_3$) → Proton Acceptor, $XCO_2R^2$ → compound 2 (with $R^{1a}O$, $R^3$, $R^4$, $R^5$, $R^6$, $NCO_2R^2$) → Proton Donor]

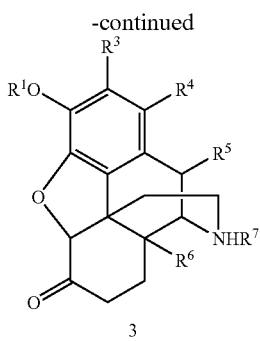

wherein:
- R¹ is selected from the group consisting of hydrogen, hydrocarbyl and substituted hydrocarbyl;
- $R^{1a}$ is an oxygen protecting group;
- R² is selected from the group consisting of alkyl and aryl;
- R³, R⁴ and R⁵, are independently selected from the group consisting of hydrogen, halogen, hydroxyl, {—}OR⁸, hydrocarbyl, and substituted hydrocarbyl;
- R⁶ is selected from the group consisting of hydrogen, halogen, hydroxyl and hydrocarbyl;
- R⁷ is selected from the group consisting of proton donors having a pKa less than about 0;
- R⁸ is selected from the group consisting of hydrocarbyl and substituted hydrocarbyl; and
- X is halogen selected from the group consisting of Cl, and Br.

18. The process of claim 17, wherein:
- R¹ is selected from the group consisting of hydrogen, acyl, alkyl, alkenyl, aryl, substituted alkyl, substituted alkenyl, substituted aryl, and alkoxycarbonyl;
- R² is alkyl;
- R³, R⁴ and R⁵ are independently selected from the group consisting of hydrogen, halogen, hydroxyl, acyl, alkyl, alkenyl, aryl, substituted alkyl, substituted alkenyl, substituted aryl, alkoxycarbonyl, carbonyl;
- R⁶ is selected from the group consisting of hydrogen, halogen, hydroxyl, alkyl and aryl;
- R⁷ is selected from the group consisting of sulfuric acid, methanesulfonic acid, toluenesulfonic acid, phosphoric acid, hydrochloric acid, and hydrobromic acid; and
- X is chloride.

19. The process of claim 17, wherein the proton acceptor has a pKa of greater than about 7; the first reaction is conducted in the presence of an aprotic solvent; the molar ratio of compound 1 to $XCO_2R^2$ to proton acceptor is from about 1:3:1 to about 1:20:20, the first reaction is conducted at a temperature ranging from about 50° C. to about 80° C.; compound 2 comprises a mixture of compounds selected from the group consisting of noroxymorphone derivatives and noroxycodone derivatives; the proton donor has a pKa less than 0; the second reaction is conducted in the presence of at least one protic solvent, the amount of protic solvent to compound 2 is about 2:1 (g/g), the molar ratio of compound 2 to proton donor is from about 1:1.5 to about 1:10 (g/g), and the second reaction is conducted at a temperature ranging from about 90° C. to about 115° C.

20. The process of claim 17, wherein the process results in the formation of side product compounds not having formula 2, and the reaction mixture separates into an organic layer, and an aqueous layer after the reaction mixture is quenched with a protic solvent.

21. The process of claim 20, wherein the side product compounds and compounds having formula 1 are removed from the reaction mixture by a wash step, the wash step comprising contacting the organic layer with a protic solvent having a pH from about 0.8 to about 2.0, followed by separation of the aqueous layer from the reaction mixture.

22. The process of claim 21, wherein the aprotic solvent is displaced with a second solvent selected from the group consisting of an alcohol having from 3 to 8 carbon atoms, and a proton donor having from 2 to 8 carbon atoms.

23. The process of claim 17, wherein compound 3 is formed as a crystal; the yield of compound 3 is from about 65% to about 85% (mol/mol); the purity of compound 3 is at least 95% as determined by chromatography.

24. The process of claim 17, wherein the optical activity of compound 1, 2, or 3 is selected from the group consisting of (−) enantiomer, (+) enantiomer, and a combination thereof.

25. The process of claim 17, wherein the configuration of carbons 5, 13, 14, and 9, respectively, of compounds 1, 2, or 3 is selected from the group consisting RRRS, RRSS, SRRS, SRSS, RSRR, RSSR, SSRR, and SSSR.

* * * * *